(12) United States Patent
Gyrn

(10) Patent No.: US 10,076,607 B2
(45) Date of Patent: Sep. 18, 2018

(54) SUBCUTANEOUS INSERTER DEVICE

(75) Inventor: Steffen Gyrn, Ringsted (DK)

(73) Assignee: UnoMedical A/S, Birkerød (DK)

( * ) Notice: Subject to any disclaimer, the term of this patent is extended or adjusted under 35 U.S.C. 154(b) by 562 days.

(21) Appl. No.: 14/008,483

(22) PCT Filed: Mar. 30, 2012

(86) PCT No.: PCT/EP2012/055803
§ 371 (c)(1),
(2), (4) Date: Feb. 5, 2016

(87) PCT Pub. No.: WO2012/131044
PCT Pub. Date: Oct. 4, 2012

(65) Prior Publication Data
US 2016/0243302 A1    Aug. 25, 2016

Related U.S. Application Data

(60) Provisional application No. 61/469,406, filed on Mar. 30, 2011.

(51) Int. Cl.
*A61M 5/158* (2006.01)
*A61M 25/06* (2006.01)

(52) U.S. Cl.
CPC ........ *A61M 5/158* (2013.01); *A61M 25/0606* (2013.01); *A61M 25/0612* (2013.01);
(Continued)

(58) Field of Classification Search
CPC .......... A61M 5/158; A61M 2005/1585; A61M 2005/1586; A61M 2005/1583; A61M 25/0606; A61M 25/0612; A61M 25/0631
See application file for complete search history.

(56) References Cited

U.S. PATENT DOCUMENTS

| | | | |
|---|---|---|---|
| 2004/0064096 A1 | 4/2004 | Flaherty et al. | |
| 2010/0030155 A1* | 2/2010 | Gyrn | A61M 5/14248 604/164.08 |
| 2012/0094214 A1 | 4/2012 | Zahid et al. | |

FOREIGN PATENT DOCUMENTS

| WO | WO 2004/011065 | 2/2004 | |
|---|---|---|---|
| WO | WO 2008029280 A2 * | 3/2008 | .......... A61M 5/2033 |
| WO | WO 2012/131044 | 10/2012 | |

OTHER PUBLICATIONS

PCT/EP2012/055803 International Preliminary Report on Patentability dated Oct. 1, 2012.
(Continued)

*Primary Examiner* — Shefali Patel
(74) *Attorney, Agent, or Firm* — UnoMedical A/S

(57) ABSTRACT

The invention relates to an inserter device for subcutaneously inserting a medical device, the inserter device comprising an outer part comprising one or more locking elements including a first locking element and one or more release elements including a first release element; a housing; and a functional part accommodated in the housing; wherein the housing comprises a sidewall with an inner surface forming a cavity, the housing extending from a first end to a second end along a first axis and comprising one or more housing guide members including a first housing guide member for engagement with one or more guide members of the functional part, and where the housing is at least partly covered by the outer part;

wherein the functional part comprises a first part with a first body extending from a first end to a second end along the first axis, the first part comprising one or more first locking members; a second part releasably connected to the first part and comprising a second body extending from a first end to a second end along the first axis, the second part comprising a second guide member and one or more second locking (Continued)

members; an insertion needle attached to the second part; an insertion spring adapted for moving the first part from a first position to a second position in an insertion direction along the first axis in relation to the housing; and a retraction spring adapted for moving the second part from the second position to a third position in an extraction direction along the first axis in relation to the housing.

15 Claims, 11 Drawing Sheets

(52) U.S. Cl.
CPC ... *A61M 25/0631* (2013.01); *A61B 2560/063* (2013.01); *A61M 2005/1583* (2013.01); *A61M 2005/1585* (2013.01); *A61M 2005/1586* (2013.01)

(56) References Cited

OTHER PUBLICATIONS

PCT/EP2012/055803 Written Opinion completed May 23, 2012.
PCT/EP2012/055803 International Search Report completed May 23, 2012.

* cited by examiner

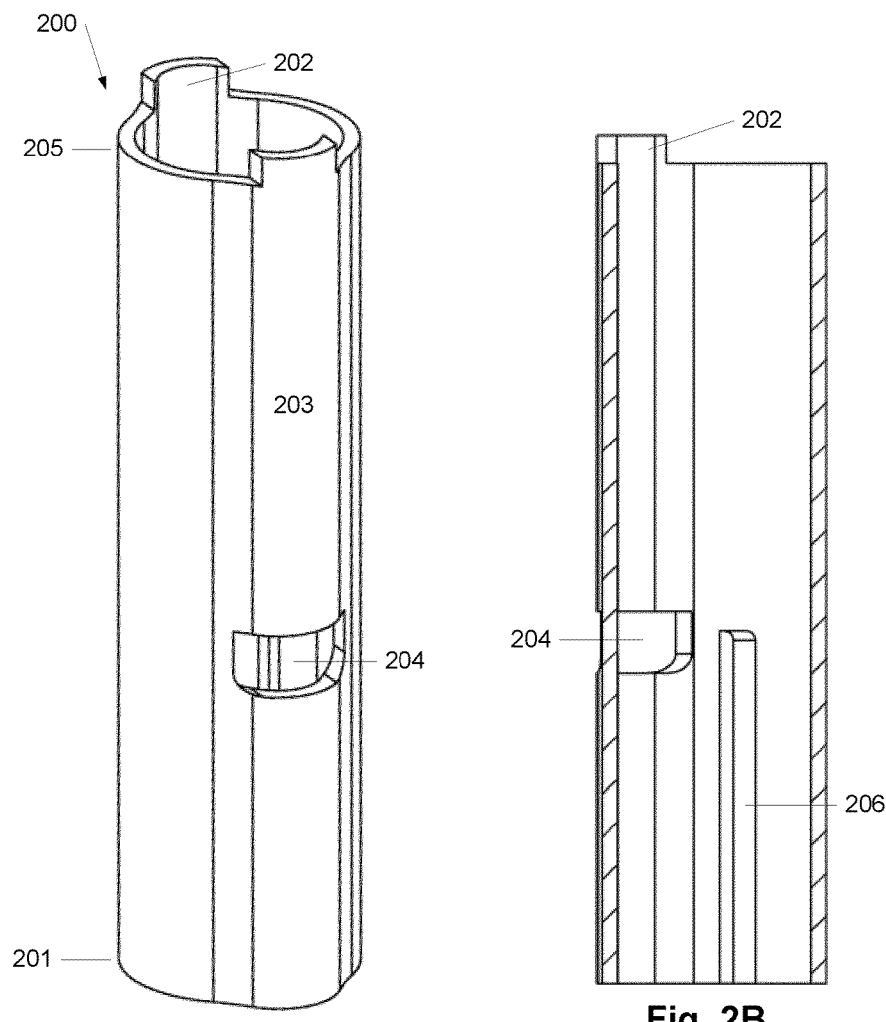

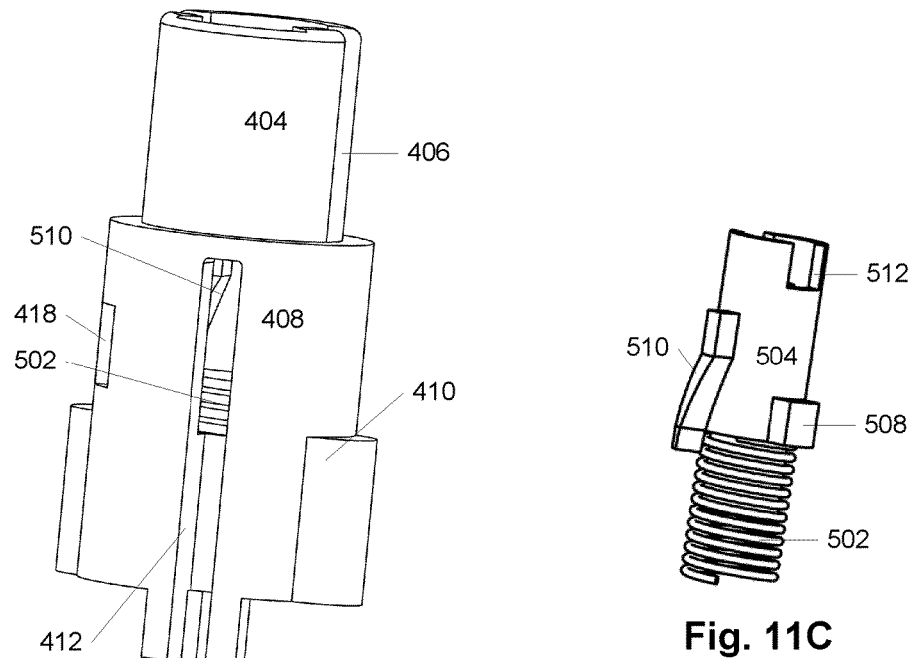
Fig. 11A
Fig. 11C
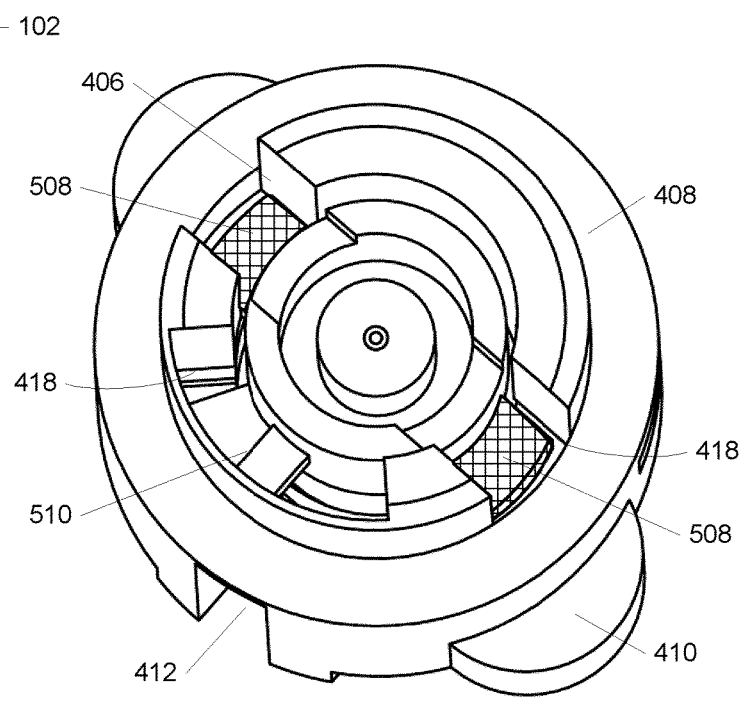
Fig. 11B

SUBCUTANEOUS INSERTER DEVICE

This application is the National Stage entry of International Application No. PCT/EP2012/055803 filed Mar. 30, 2012, which claims priority to U.S. Provisional Application No. 61/469,406 filed Mar. 30, 2011, both of which are incorporated herein by reference in their entireties.

The present disclosure relates to an inserter device for inserting a medical device subcutaneously comprising an outer part, a housing, and a functional part.

An inserter device also called inserter or injector is commonly used in the medical field for inserting medical devices, such as infusion sets, sensors or the like, through the skin of a patient in a more or less automated fashion.

Commonly, when using an inserter, the user, i.e. the patient or the treatment provider e.g. nurse, doctor, relative, or the like has to apply a force towards the surface of the skin of the patient in order to provide injection of the medical device or a part of the medical device having the form of a needle, a cannula, a sensor, or the like. This can cause physiological or psychological distress and/or discomfort, and may lead to inappropriate application of the medical device. Many people are afraid of sharp objects, such as injection needles and other penetrating devices, commonly used for medical treatment and therapy. This fear is often irrational, and it may hamper an appropriate medical treatment. For example in the case of self-medication, a lack of administration of an appropriate dose of a required medical composition can lead to complications, which may even be life-threatening. When treating diabetes, e.g. in juveniles, there is a risk that the required insulin-dose may not be self-administered due to irrational fear of the insertion needle, combined with a general lack of knowledge and awareness concerning the consequences of omitting the correct application of the device and dosage.

A further known issue with insertion of medical devices is the risk of contamination of the penetrating member before or during application. This can easily lead to the introduction of an infection to a patient, e.g. through a contaminated insertion needle. The longer such a needle is exposed, the higher the risk of accidental contamination, e.g. by touching the needle with a finger, bringing the needle in contact with an unclean surface, or by airborne contamination, aerosol contamination and the like. Depending on the nature of the contamination (e.g. comprising virus, bacteria, fungus, yeast and/or prion) combined with the general health status of the patient, the resulting infection can rapidly turn into a life threatening situation.

Finally, it is well known that contact with an infected, used needle especially in hospital environments can be life-threatening, and the risk of accidental exposure to contaminated material in the form of a used insertion needle must be minimized.

Thus, there is an obvious need in the art for a robust, reliable, accurate, safe, hygienic, and user friendly inserter device, which addresses the issues discussed above.

DESCRIPTION

Disclosed herein is an inserter device for subcutaneously inserting a medical device, the inserter device comprising an outer part comprising one or more locking elements including a first locking element and one or more release elements including a first release element; a housing; and a functional part accommodated in the housing; wherein the housing comprises a sidewall with an inner surface forming a cavity, the housing extending from a first end to a second end along a first axis and comprising one or more housing guide members including a first housing guide member for engagement with one or more guide members of the functional part, and where the housing is at least partly covered by the outer part; wherein the functional part comprises a first part with a first body extending from a first end to a second en along the first axis, the first part comprising one or more first locking members; a second part releasably connected to the first part and comprising a second body extending from a first end to a second end along the first axis, the second part comprising a second guide member and one or more second locking members; an insertion needle attached to the second part; an insertion spring adapted for moving the first part from a first position to a second position in an insertion direction along the first axis in relation to the housing; and a retraction spring adapted for moving the second part from the second position to a third position in an extraction direction along the first axis in relation to the housing; wherein the first housing guide member and the second guide member are configured for rotating the second part about the first axis when the first part is moved from the first position to the second position, whereby the second part is moved from a locked position to an unlocked position relative to the first part.

By guide member/element is meant a protrusion a recess, channel and/or slit. By locked position is meant a position wherein the second part is prevented from moving relative to the first part in the direction of retraction and by an unlocked position is meant a position wherein the second part can move relative to the first part in the direction of retraction, thus away from the first part.

The rotating of the second part such that it is moved from a locked position to an unlocked position relative to the first part provides a simplified inserter device constituting a minimum of separate parts. This is advantageous in relation to production costs.

Other embodiments and advantages are provided below in the detailed description, in the claims and in the drawings.

BRIEF DESCRIPTION OF THE DRAWINGS

An embodiment of the inserter device is displayed in the figures, wherein:
FIGS. 2A-C show the housing of the inserter device;
FIG. 11A-C show the first part and the second part of FIGS. 10A-C in an unlocked position immediate prior to retraction of the insertion needle.

DETAILED DESCRIPTION

Figure 1:
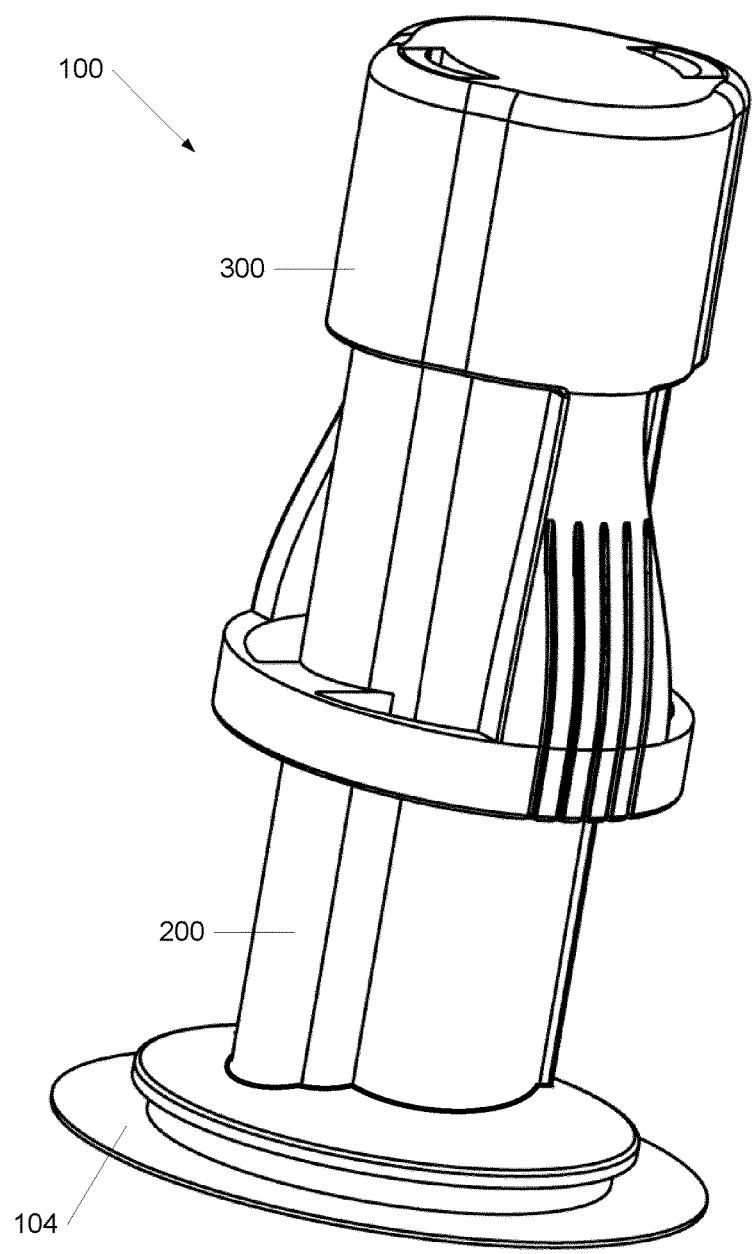
FIG. 1 show the assembled inserter device.

FIG. 1 shows an embodiment of an inserter device 100 having automatic insertion and automatic retraction of an insertion needle 102. The inserter device 100 is used for placing a port site 104 combined with a subcutaneous part 106 (see FIGS. 7-9) subcutaneously in a patient. The port site 104 can be used for injecting portions of medication over a period of normally up to 3 days. The port site 104 can be e.g. an infusion device, a sensor device, patch devices or similar.

The inserter device 100 is displayed in FIG. 1 in an assembled shelf state and comprises an outer part 300 and a housing 200, where the housing 200 is partly covered by the outer part 300. Accommodated inside the housing 200 is a functional part which comprises:
 a first part 400;
 a second part 500;
 an insertion spring 402;
 a retraction spring 502; and
 an insertion needle 102 attached to the second part 500.

The inserter part 100 is shown with a port site 104 being an infusion device attached, but other port sites could also be used.

Throughout the description 'distal' will refer to the end/surface/element furthest away from the port site 104 and 'proximal' will refer to the end/surface/element closest to the port site 104. The 'vertical' plane/direction will refer to the plane/direction extending parallel with the insertion needle 102 and the 'horizontal' plane/direction will refer to the plane/direction parallel with the patients skin surface, thus perpendicular to the vertical plane/direction.

FIG. 2A shows the housing 200 in a front view, FIG. 2B the housing 200 in a cut-through view along the axis J-J, and FIG. 2C the housing 200 in a view from the proximal end 201 of the housing 200. The shape and/or diameter of the proximal end 201 can have different designs depending on the site port 104 attached to the proximal end 201, and the invention is therefore not limited to the shown embodiment.

The housing 200 constitutes an elongated tube comprising a sidewall 203 with an inner surface forming a cavity. The housing 200 has in an oval shape ensuring that the first part 400 cannot rotate in the horizontal plane before, during or after activation of the insertion device 100.

The housing 200 comprises two proximal protrusions 202, which are positioned opposite one another at the distal end 205 of the housing 200. The proximal protrusions 202 are adapted for engaging with two corresponding openings 304 in the outer part 300. The housing 200 further comprises two openings 204, which are positioned horizontally opposite one another approximately in the middle of the housing 200. The openings 204 are adapted for engaging with locking elements 312 on the outer part 300. The proximal protrusions 202 and the openings 204 are aligned pair wise along vertical axes extending from the proximal end 203 to the distal end 205, thus extending in a direction parallel to the direction of insertion.

On the inside of the housing 200, there is a housing guide member 206 extending from proximal end 203 and to approximately the middle of the housing 200. The housing guide member 206 extends along an axis parallel to the axis defined by the pair wise proximal protrusions 202 and openings 204 displaced approximately 80-110 degrees in relation thereto. The housing guide member 206 is adapted for engaging inside a slit 412 in the first part 400, and is dimensioned such that when it engages inside the slit 412, part of it extends through the slit 412 and inside into the inside of the first part 400.

Figure 3A:
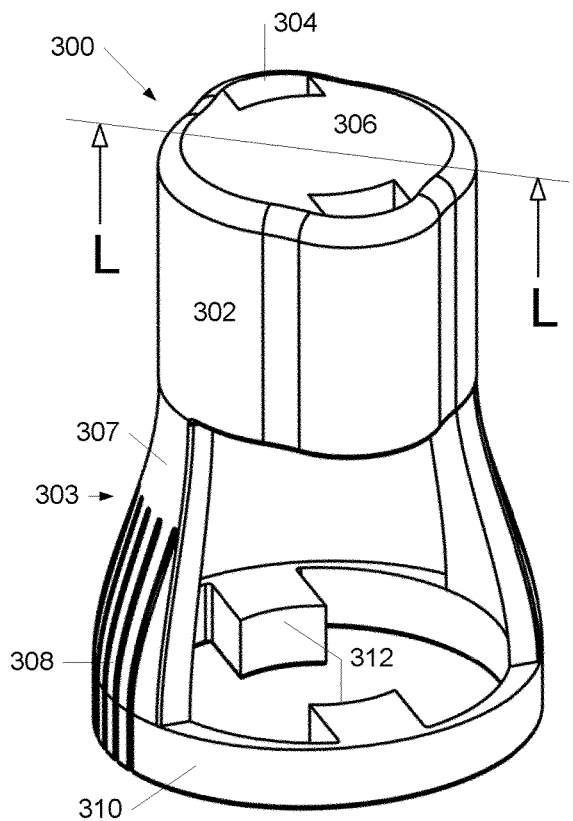
FIGS. 3A-B show the outer part of the inserter device.
Figure 3B:
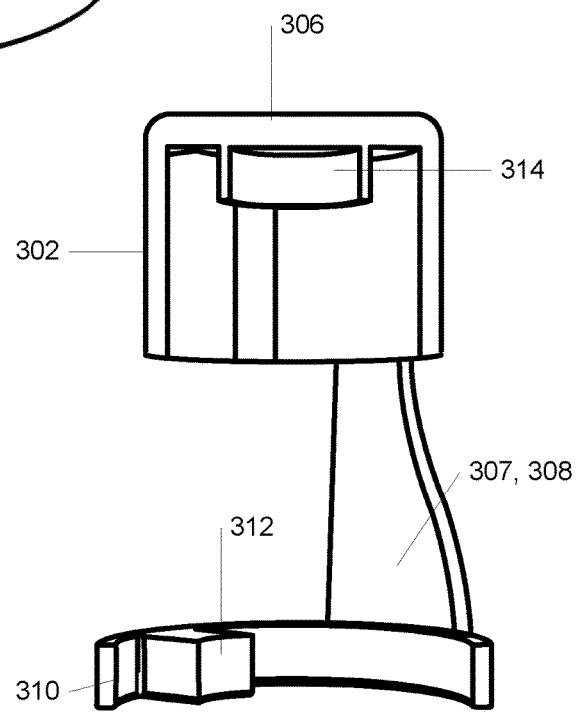

FIG. 3A shows the outer part 300 in a front on view and FIG. 3B shows the outer part 300 in a cut-through view along the axis L-L. The outer part 300 constitutes a first section 302 and a second section 303.

The first section 302 comprises two openings 304 at the distal end 306 of the first section 302. The two openings 304 are adapted for engaging with the corresponding proximal protrusions 202 of the housing 200, thereby interlocking the housing 200 and the outer part 300. On the inside of the distal end 306 there is a protruding annular collar 314 where around the distal end of the insertion spring 402 is positioned. This ensures that the insertion spring 402 cannot be displaced horizontally before, during and/or after insertion and/or retraction of the insertion needle 102.

The second section 303 comprises two outwardly extending arms 307, an engaging device 310, release elements 308, and locking elements 312. The extending arms 307 are positioned opposite one another in the horizontal plane and are directly attached to the first section 302 at their distal end. The engaging device 310 is in this embodiment a ring, which can be either circular or oval. Other shapes could also be imagined. The release elements 308 extend partly on the outwardly extending arms 307 and partly on the engaging device 310.

The locking elements 312 are in this embodiment two inwardly pointing parts for engaging with the openings 204 in the housing 200. The locking elements 312 are positioned opposite one another on the engaging device 310 and are displaced approximately 90 degrees in relation to the release elements 308 and the arms 303. The locking elements 312 ensures that the insertion spring 402 stays in a pre-loaded position before activation of the inserter device 100 by engaging with locking members 410 on the first part 400, thereby fixing the first part 400 at the top of the distal end 205 of the housing 200, thus at a position on top of the locking elements 312.

Figure 4A:
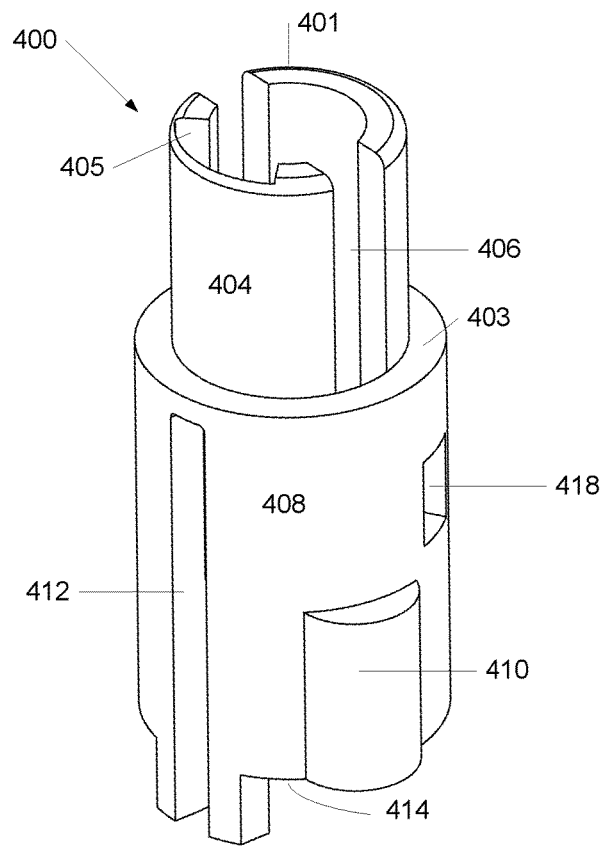
FIGS. 4A-C show the first part of the inserter device.
Figure 4B:
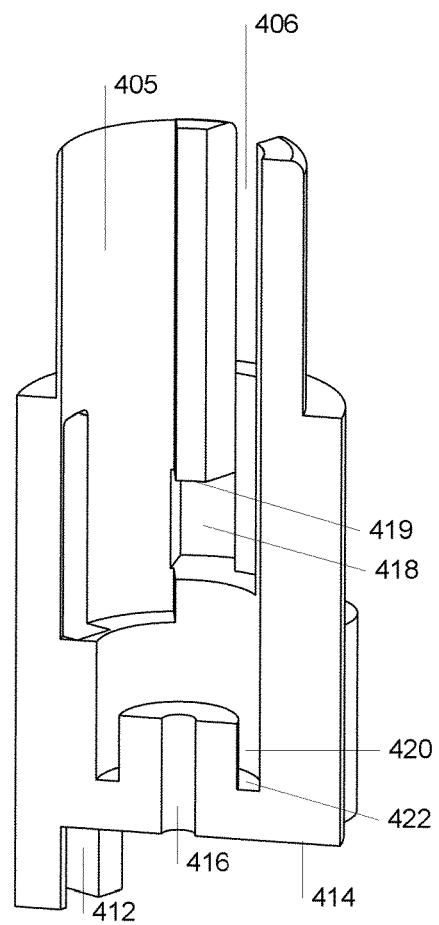
Figure 4C:
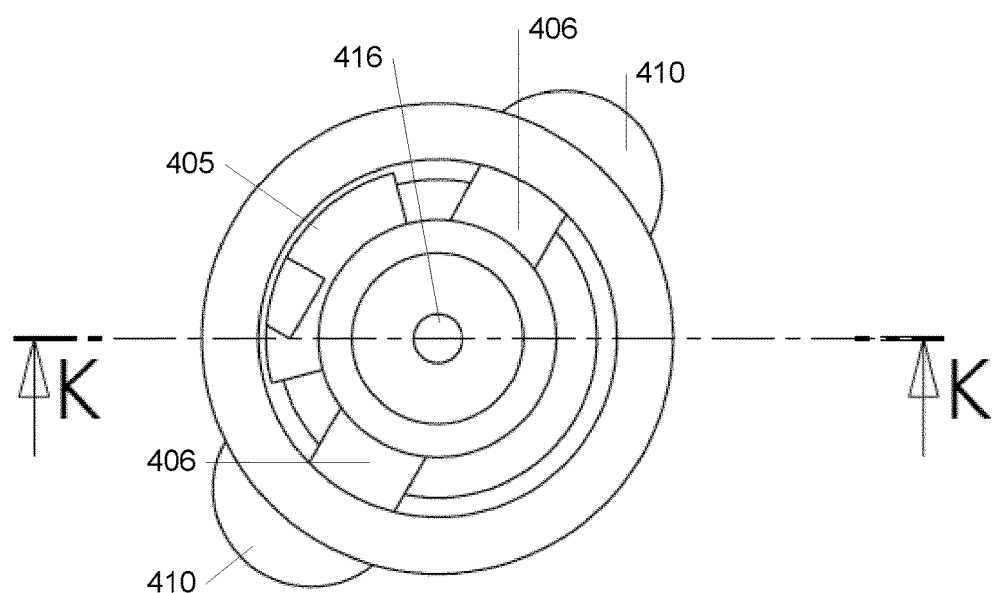

FIG. 4A shows the first part 400 in a front view, FIG. 4B the first part 400 in a cut-through view along the axis K-K, and FIG. 4C the first part 400 in view from the distal end 401 of the first part 400.

The first part 400 constitutes a tube comprising a first section 404 and a second section 408, where the outer diameter of the first section 404 is smaller than the outer diameter of the second section 408, thereby forming a support surface 403, whereupon the insertion spring 402 rests at one end.

The first section 404 comprises two releasing slits 406 for engaging with corresponding locking members 508, 508' on the second part 500. The releasing slits 406 extends from the distal end 401 to the distal surface 407 of the proximal end 409 along a vertical axis parallel to the insertion direction. The first section 404 further comprises a recess 405 on the inner surface facilitating space for an inclining guide member 510 on the second part 500.

The second section 408 has locking members 410 (in this embodiment two protrusions) placed opposite one another in the horizontal plane on the outside of the second section 408. In the pre-loaded shelf position shown in FIG. 7, the locking members 410 are engaging with the locking elements 312 of the outer part 300. This secures the insertion spring 402 in the pre-loaded position preventing the insertion needle 102 from being activated during transportation. Between the two locking members 410 is a slit 412 for receiving the inner housing guide member 206 of the housing 200 during activation of the inserter device 100.

The proximal surface 414 of the first part 400 is provided with a central annular opening 416 (see FIG. 7) where through the insertion needle 102 can pass when inserting the subcutaneous part 106 in a patient. The opening 416 is normally so small that it only allows the insertion needle 102 to pass through, thus the diameter of the opening 416 is normally 10-20% larger than the diameter of the insertion needle 102. This is advantageous as it is prevents a user from accidentally putting a finger through the opening 416 and e.g. get in contact with the used insertion needle 102. Further, by having a very small opening 416, the insertion needle 102 is hardly visible, which has a positive psychological effect on patients/users that are afraid of needles.

On the inside of the second section 408 are found openings 418 for engaging with corresponding locking members 508, 508' on the second part 500. In the shelf and the insertion position, the locking members 508, 508' on the second part 500 are supported by a support rim 419, thereby fixing the retraction spring 502 and the second part 500 in the pre-loaded state. On the distal surface 422 of the proximal end 421 is an annular recess 420 (see FIG. 7) accommodating one end of the retraction spring 502, thereby ensuring that it cannot be displaces horizontally before, during and/or after insertion and/or retraction.

Upon insertion of the insertion needle 102, the proximal surface 414 exercise a pressure on the subcutaneous part 106 locking the subcutaneous body part 110 inside the opening of the port site 104. Further, as the first part 400 after insertion of the insertion needle 102 is pressing against the distal surface 114 of the subcutaneous part 106 due to the relaxed insertion spring 402, the proximal surface 414 assists in releasing the subcutaneous part 106 from the insertion needle 102 as the insertion needle 102 is extracted into the inserter device 100.

Optionally, the first part 400 can be provided with additional means (not shown in the figure) for releasing the subcutaneous part 106 from the insertion needle 102. These means for releasing the subcutaneous part 106 can have the form of a distance piece, which assures that the subcutaneous part 106 is pushed down into the opening of the base 104 with such a force that the subcutaneous part 106 can get past or get in contact with a locking mechanism inside the opening of the base 104. In one embodiment, the means for releasing the subcutaneous part 106 comprises a flat spring placed between the proximal surface 414 of the first part 400 and the distal surface 114 of the subcutaneous part 106. The flat spring is attached to or is a part of the first part 400 at one end. As the first part 400 is pushed down towards the base 104 by the insertion spring 402, the flat spring will be loaded as the first part 400 gets close enough to the base 104. The flat spring will then exercise a pressure on the subcutaneous part 106 locking the subcutaneous body part 100 inside the opening of the base 104.

Figure 5A:
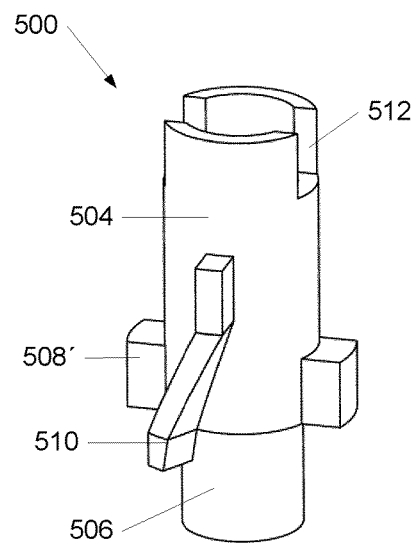
FIGS. 5A-B show the second part of the inserter device.
Figure 5B:
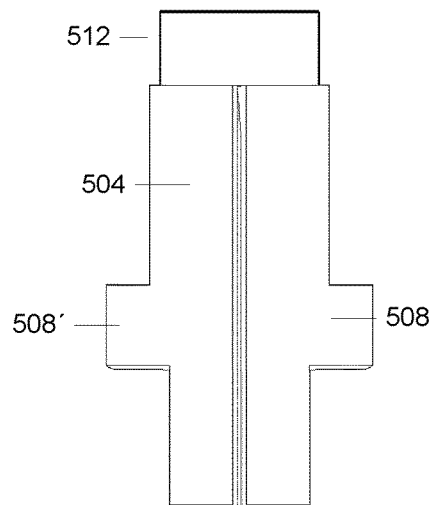
Figures 10A, 10B, 10C:
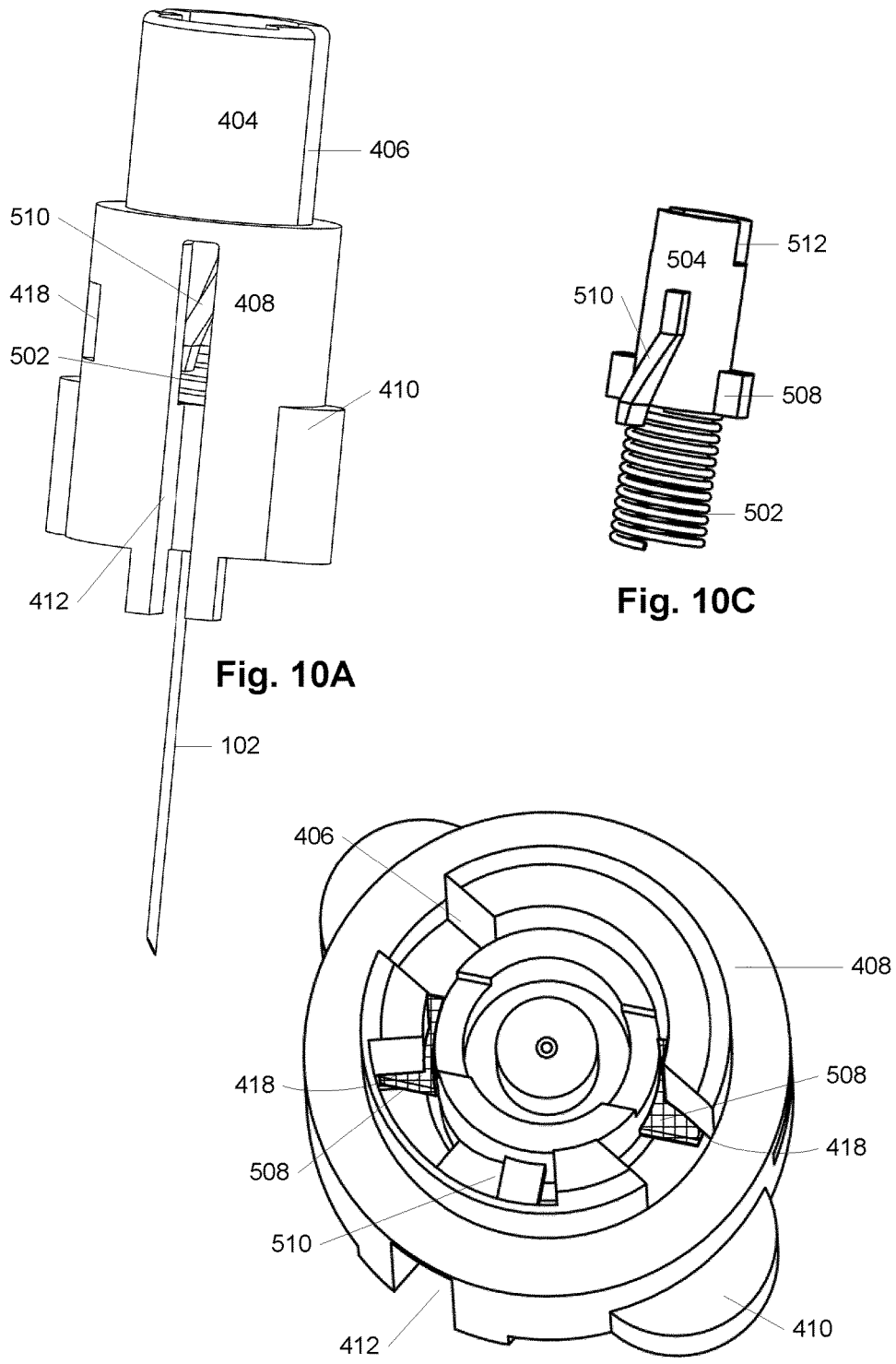
FIG. 10A-C show the first part and the second part in a interlocked position subsequent to insertion of an insertion needle.

FIG. 5A shows the second part 500 in a front view and FIG. 5B the second part 500 in a cut-through view along the axis connecting the locking members 508, 508', 508'. The second part 500 constitutes a small elongated tube which can fit inside the first part 400. The second part 500 comprises a first section 504 and a second section 506, where the outer diameter of the first section 504 is larger than the diameter of the second section 506, thereby accommodating a support surface 503 for one end of the retraction spring 502 as shown in FIGS. 10C and 11C, which ensures that the retraction spring 502 remains positioned around the second section 506 at one end at all time.

On the outside of the first section 504 are locking members 508, 508' (in this embodiment two protrusions) which slide inside the corresponding releasing slits 406 in the first part 400 during activation of the inserter device 100. In between the locking members 508, 508' is the inclining guide member 510. The second part 500 further comprises recesses 512 for guiding the second part 500 in position inside the first part 400 during manufacturing of the inserter device 100. The insertion needle 102 is attached to the second part 500 and extends up inside the normally solid second part 500.

The position of the second part 500 inside the first part 400 is only an embodiment of the invention. The reverse could also be imagined.

Figure 6:
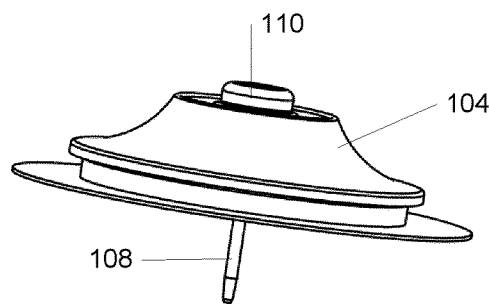
FIG. 6 shows an embodiment of a port site.

FIG. 6 shows en embodiment of a port site 104 being an infusion port wherein a subcutaneous part 106 comprising a cannula 108 and a body part 110 has been insertion. The body part 110 is shaped such that it secures the subcutaneous part 106 in the port site 104 upon insertion of the subcutaneous part 106 in a patients skin 112. The subcutaneous part 106 is positioned on the insertion needle 102 and is kept in position due to the friction between the insertion needle 102 and the soft contact parts of the subcutaneous part 106 such as the cannula 108. The insertion needle 102 can be located inside, alongside or outside the cannula 108.

Figure 7:
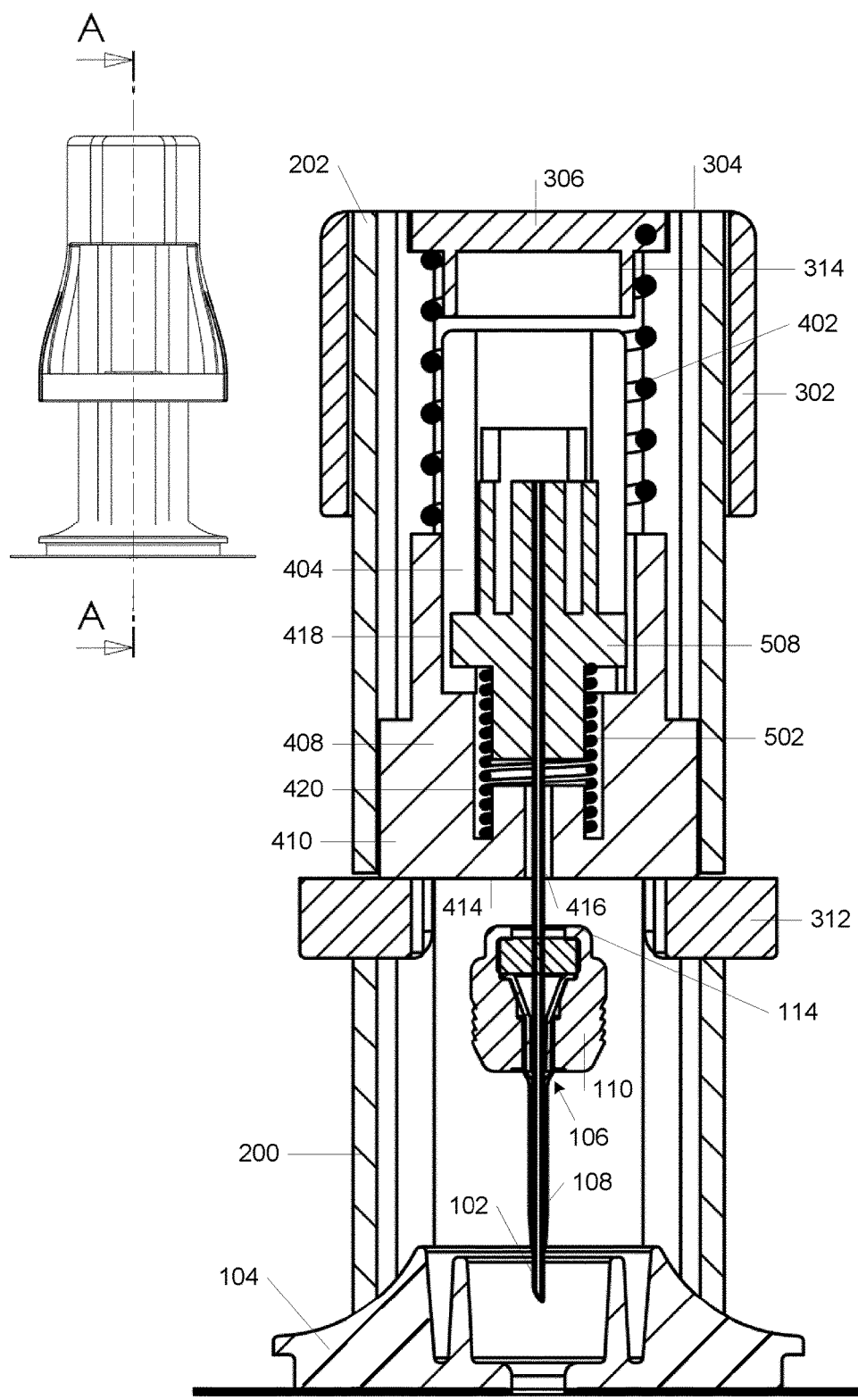
FIG. 7 shows a cut-through view of the inserter device in a shelf position.
Figure 8:
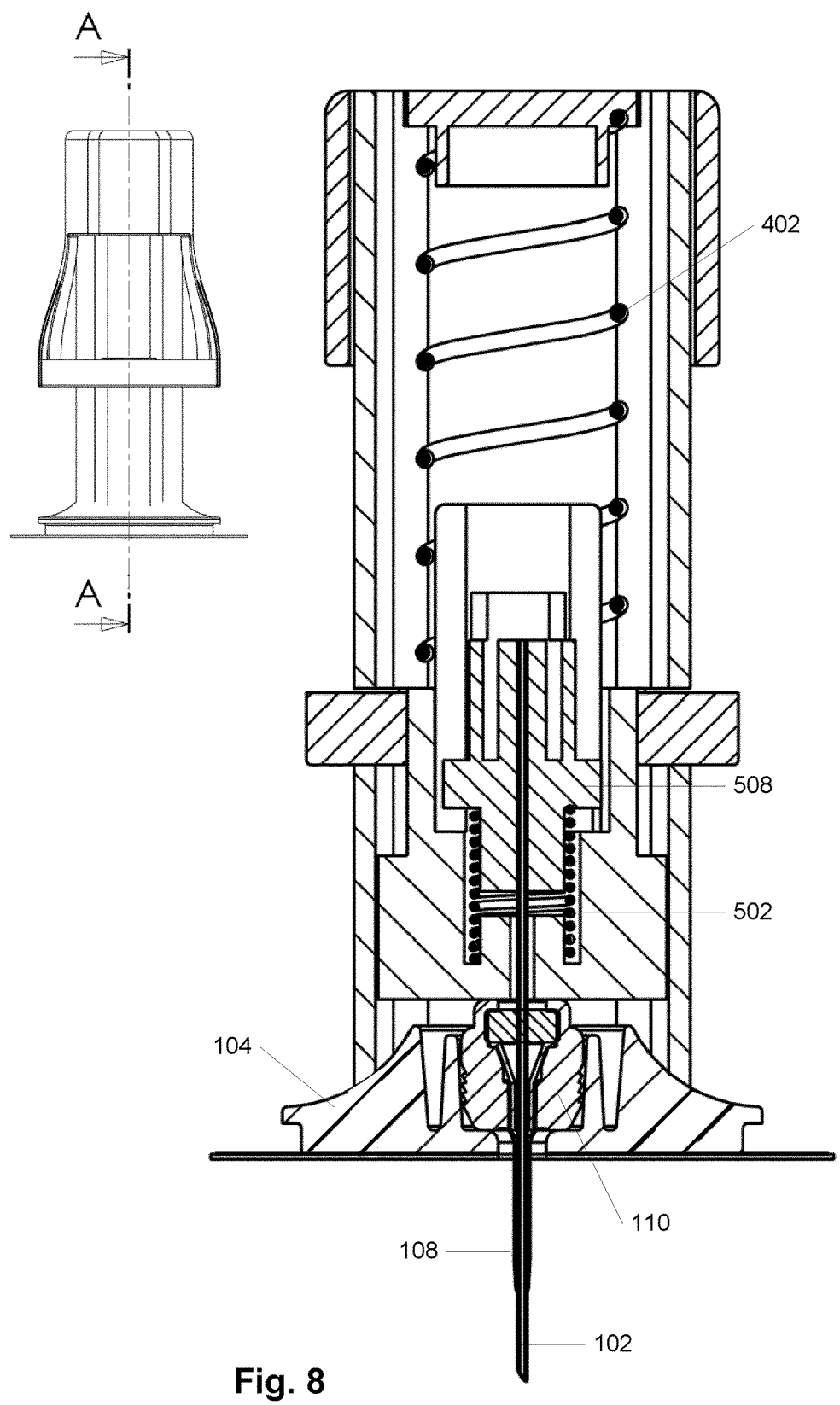
FIG. 8 shows a cut-through view of the inserter device in an inserted position.
Figure 9:
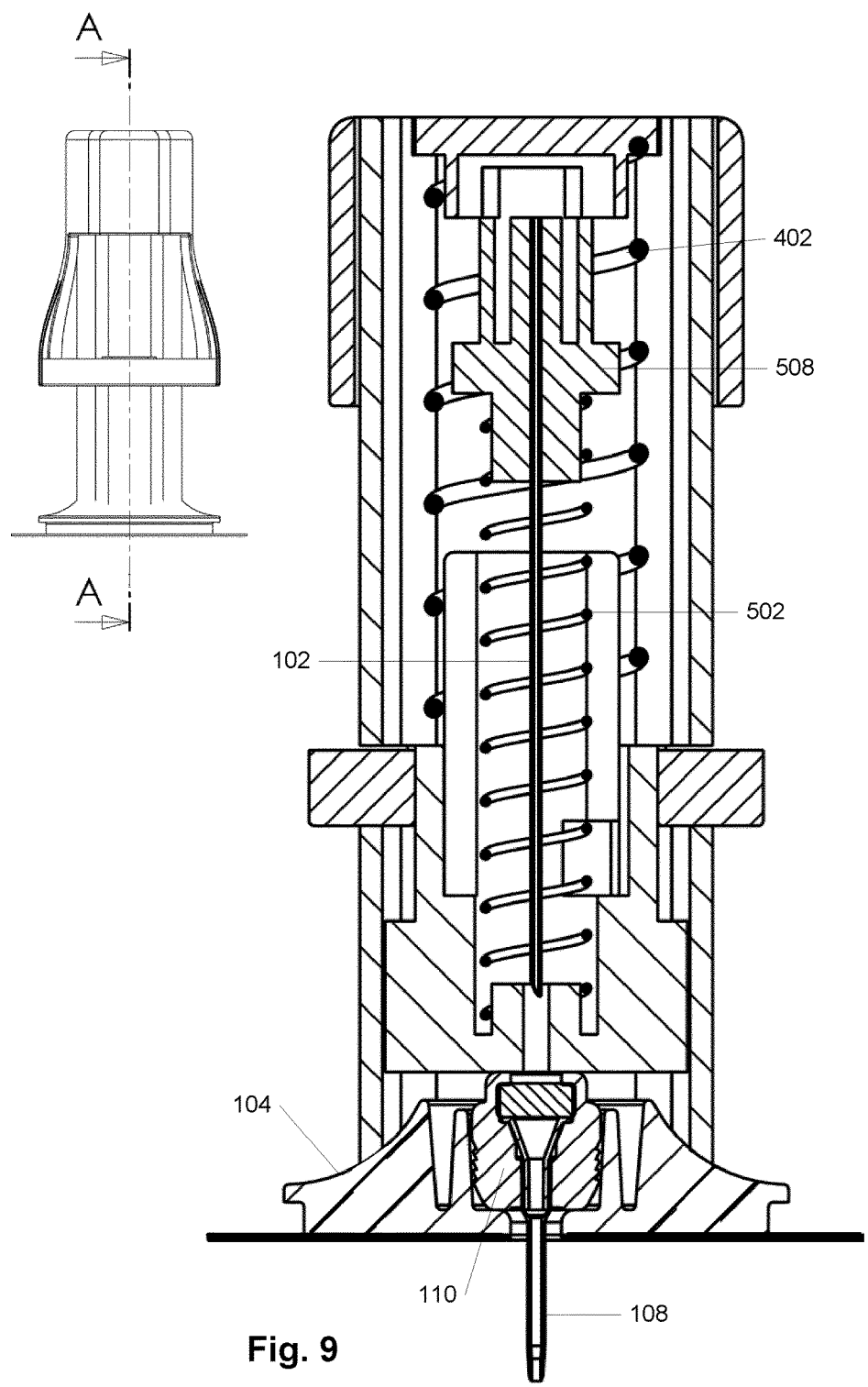
FIG. 9 shows a cut-through view of the inserter device in a retracted position.

In FIG. 7-9, the inserter device 100 is displayed in a cut-through view along line A-A. In here, the different parts 200, 300, 400, 500 interlocking with one another can be seen more clearly.

Normally, the four parts constituting the inserter device 100, i.e. the housing 200, the outer part 300, the first part 400, and the second part 500, are constructed from a hard plastic possibly combined with sections of a softer material preventing the parts from breaking during activation of the inserter device 100. The insertion spring 402 and the retraction spring 502 are normally metal springs, but other types of materials such as e.g. plastic could also be used.

FIG. 7 shows the inserter device 100 in a shelf state before activation of the inserter device 100. Both springs 402, 502 are in a pre-loaded position; The insertion spring 402 and first part 400 are secured in the pre-loaded shelf position by the locking elements 312 preventing the first part 400 from being displaced in relation to the housing 200. The second part 500 is kept in the pre-loaded shelf position by the locking members 508, 508', which are engaging with the two openings 418 and the support rim 419 on the inside of the first part 400.

The pre-loading of the two springs 402, 502 in the shelf state ensures an advantageous compact design of the inserter device 100.

FIG. 8 shows the inserter device 100 in the inserted position where the cannula 108 has been inserted into the patients skin 112 and the body part 110 secured inside the port site 104. Normally the port site 104 has an adhesive surface, which is used for attaching the port site 104 releasably to the patients skin 112. A release paper has to be removed from the port site 104 prior to placing it on the patients skin 112. In the inserted position shown in FIG. 8, the insertion needle 102 is still inserted in the patient, thus it has not returned to a retracted position yet. The insertion spring 402 is in a relaxed position, whereas the retraction spring 502 is still in the pre-loaded position.

FIG. 9 shows the inserter device 100 in a retracted position after the cannula 108 has been inserted into the patients skin 112 and the insertion needle 102 attached to the second part 500 has been retracted to a position at the distal end 205 of the housing 200, i.e. no longer positioned inside the first part 400. The retraction spring 502 is in the relaxed position from where it cannot be re-loaded again without breaking apart the inserter device 100. This ensures that the insertion needle 102 is contained inside the inserter device 100 unable to extend out of it.

Insertion of the subcutaneous part 106 into a patients skin 112 is done by placing the inserter device 100 on the patients skin 112 with the port site 104 positioned directly on top of the patients skin 112, and then activating the inserter device 100. Normally, a protective release paper has to be removed from the port site 104 prior to placing it on the patients skin 112, thereby exposing an adhesive layer underneath the port site 104 for fastening the port site 104 to the patients skin 112.

Activation of the inserter device 100 is done by applying a pressure on the two release elements 308 on the outer part 300, i.e. deforming the engaging device 310 by pressing the two release elements 308 closer together. The distance between the locking elements 312 thereby increases such that there is enough space to allow for the locking members 410 on the first part 400 to pass by the locking elements 312 at the aid of the insertion spring 402, the latter which in this manner is allowed to relax.

When the insertion spring 402 relaxes, the first part 400 containing the second part 500 and the inserter needle 102 is pressed towards the port site 104, thereby inserting the cannula 108 in the patients skin 112. As the first part 400 progress towards the port site 104, the housing guide member 206 travels inside the slit 412 of the first part 400. Behind the slit 412, the inclining guide member 510 on the second part 500 is positioned, and as the inner housing guide member 206 extending into the first part 400 progresses inside the slit 412, the inner wall 412 comes in contact with the inclining guide member 510 forcing the second part 500 to rotate in a clock-wise direction in the horizontal plane. As a consequence, the locking members 508, 508' on the second part 500 are released from the inner openings 418 of the first part 400 and the second part 500 is pushed in a direction away from the port site 104 by the aid of the retraction spring 502, the latter which in this manner relaxes.

The interaction between the second part 500 and the first part 400 resulting in the release of the second part 500 from the first part 400 after the insertion of the cannula 108 in the patients skin 112 is illustrated in FIGS. 10A-C and FIGS. 11A-C, where FIGS. 10A-C show the first part 400 and the second part 500 in the interlocked position prior to release of the second part 500, and FIGS. 11A-C show the first part 400 and the second part 500 in the unlocked position subsequently triggering the release of the second part 500.

In FIG. 10A and FIG. 11A, the first part 400 and the second part 500 are shown in a front on angle, wherein the inclining guide member 510 positioned behind the slit 412 is clearly seen. FIGS. 10C and 11C show the second part 500 and the retraction spring 502 from the same front on angle as in FIGS. 10A and 11A, respectively. FIGS. 10B and 11B show the first part 400 and the second part 500 in a perspective top view, wherein the interaction between the openings 418 on the inside of the first part 400 and the locking members 508, 508' on the outside of the second part 500 are clearly seen.

The clock-wise turning of the second part 500 prompt by the housing guide member 206 progressing inside the slit 412 and turning the inclining guide member 510 is observable when comparing FIGS. 10A-C and FIGS. 11A-C, in particular the A and B figures. The release of the locking members 508, 508' from the inner openings 418 is seen most clearly in the C figures, where FIG. 10C shows the locking members 508, 508' being secured underneath the inner openings 418, and FIG. 11C shows the locking members 508, 508' positioned in the releasing slits 406 in first part 400, allowing the retraction spring 502 to relax and thereby push the second part 500 to an extracted position, where it is no longer contained inside the first part 400.

The second part 500 is normally turned 10-40 degrees in relation to the first part upon release of the second part 500 form the first part 400.

The inserter device 100 is constructed such that it can only be used once, since it is impossible to re-load the springs 402, 502 after activation of the inserter device 100. This is advantageous as the user cannot be tempted to use the device more than once and thereby expose him/her self to an unnecessary health risk.

Construction of the inserter device 100 from essentially four interconnected parts 200, 300, 400, 500 combined with two springs 402, 502 and an insertion needle 102 allows for a simple construction, whereby a rather compacted device is obtained. This reduces production costs.

Normally, the inserter device 100 is contained in a protective bag during transportation. The conditions inside the bag are sterile ensuring that the inserter device 100 can be kept sterile up until the time where it is going to be used.

The only time, the inserter needle 102 is exposes is in the brief moment of insertion. This makes the inserter device 100 safe to handle as the user cannot get in contact with the insertion needle 100 prior to activation of the device and/or after the automatic retraction of the insertion needle 100. It is thereby safe to dispose the inserter device 100 along with ordinary household waste without protecting it before hand.

The automatic insertion and automatic retraction of an insertion needle 102, prompt by applying a pressure in the horizontal plane, is easy to perform by the user, since it essentially involves one action. Further, as the insertion process does not involve applying a pressure in the direction towards to skin, the procedure is more appealing to users, that have a fear of injection needles and other penetrating devices, as these user often find it significantly more difficult to insert an insertion needle if they have to apply a pressure towards the skin at the same time.

LIST OF REFERENCES 100 inserter device
102 insertion needle
104 port site
106 subcutaneous part
108 cannula
110 body part of the subcutaneous part
112 patients skin
114 distal surface of the body part of the subcutaneous part
200 housing
201 proximal end of the housing
202 proximal protrusions on the housing
203 sidewall of the housing
204 openings in the housing
205 distal end of the housing
206 housing guide member inside the housing
300 outer part
302 first section of the outer part
303 second section of the outer part
304 openings in the outer part
306 distal end of the outer part
307 outwardly extending arms of the outer part
308 release element of the engaging device
310 engaging device of the outer part
312 locking element of the engaging device
314 annular collar on the inside of the outer part
400 first part
401 distal end of the first part
402 insertion spring
403 support surface of the first part 404 first section of the first part
405 recess in the first part
406 releasing slit in the first part
407 distal surface of the proximal end of the first part
408 second section of the first inner part
409 proximal end of the first part
410 protrusions in the first part
412 slit in the first part
414 proximal surface of the first part
416 central opening in the proximal surface
418 openings in the first part
419 support rim of the first part
420 annular recess in the distal surface of the first part
421 proximal end of the first part
422 distal surface of the proximal end of the first part
500 second part
502 retraction spring
503 support surface of the second part
504 first section of the second part
506 second section of the second part
508 locking members on the second part
508' locking members on the second part
510 inclining guide member on the second part
512 recesses in the second part

The invention claimed is:

1. An inserter device for subcutaneously inserting a medical device, the inserter device comprising:
   an outer part (300) comprising one or more locking elements including a first locking element (312) and one or more release elements including a first release element (308);
   a housing (200); and
   a functional part accommodated in the housing;
   wherein the housing comprises a sidewall (203) with an inner surface forming a cavity, the housing extending from a first end to a second end along a first axis and comprising one or more housing guide members including a first housing guide member (206) for engagement with one or more guide members of the functional part, and where the housing is at least partly covered by the outer part;
   wherein the functional part comprises:
      a first part (400) with a first body extending from a first end to a second end along the first axis, the first part comprising one or more first locking members (410);
      a second part (500) releasably connected to the first part and comprising a second body extending from a first end to a second end along the first axis, the second part comprising a second guide member (510) and one or more second locking members (508, 508');
      an insertion needle (102) attached to the second part;
      an insertion spring (402) adapted for moving the first part from a first position to a second position in an insertion direction along the first axis in relation to the housing; and
      a retraction spring (502) adapted for moving the second part from the second position to a third position in an extraction direction along the first axis in relation to the housing;
   wherein the first housing guide member and the second guide member are configured for rotating the second part about the first axis when the first part is moved from the first position to the second position, whereby the second part is moved from a locked position to an unlocked position relative to the first part.

2. The inserter device according to claim 1, wherein the first locking element is two protrusions positioned on an annular engaging device extending inwards.

3. The inserter device according to claim 2, wherein the first release element is two surfaces positioned on the annular engaging device.

4. The inserter device according to claim 2, wherein the one or more first locking members (410) are protrusions on an outer surface of the first part.

5. The inserter device according to claim 1, wherein the first housing guide member is a wall extending from the sidewall into the cavity of the housing.

6. The inserter device according to claim 1, wherein the second guide member (510) is an inclining sidewall extending outwardly from an outer surface of the second part.

7. The inserter device according to claim 1, wherein the one or more second locking members (508, 508') are protrusions extending outwardly from an outer surface of the second part.

8. The inserter device according to claim 1, wherein the outer part comprises an annular collar on an inside of the outer part, where the insertion spring at a first end encircles the annular collar.

9. The inserter device according to claim 1, wherein the insertion spring at a second end encircles an outer part of the first part.

10. The inserter device according to claim 1, wherein the first part comprises an annular recess on an inside of the first part for supporting the retraction spring at a first end.

11. The inserter device according to claim 1, wherein the retraction spring at a second end encircles an outer part of the second part.

12. The inserter device according to claim 1, wherein the medical device comprises a port site and a subcutaneous part for engaging inside an opening in the port site upon subcutaneous insertion of the medical device.

13. The inserter device according to claim 12, wherein the first part when in the second position exercises a pressure on the subcutaneous part thereby locking the subcutaneous part inside the opening of the port site.

14. The inserter device according to claim 13, wherein the first part when the second part is in the third position exercises a pressure on the subcutaneous part thereby preventing the subcutaneous part from departing from the port site upon extraction of the insertion needle.

15. The inserter device according to claim 12, wherein the first part when the second part is in the third position exercises a pressure on the subcutaneous part thereby preventing the subcutaneous part from departing from the port site upon extraction of the insertion needle.

* * * * *